United States Patent [19]

Greer

[11] Patent Number: 5,627,276

[45] Date of Patent: May 6, 1997

[54] PEROXIDE DEGRADATION OF DNA FOR VISOCITY REDUCTION

[75] Inventor: William Greer, Billingham, United Kingdom

[73] Assignee: Zeneca Limited, London, England

[21] Appl. No.: 424,458

[22] PCT Filed: Oct. 27, 1993

[86] PCT No.: PCT/GB93/02208

§ 371 Date: Apr. 27, 1995

§ 102(e) Date: Apr. 27, 1995

[87] PCT Pub. No.: WO94/10289

PCT Pub. Date: May 11, 1994

[30] Foreign Application Priority Data

Oct. 27, 1992 [GB] United Kingdom .................. 9222561

[51] Int. Cl.$^6$ .................. C07H 1/00; C07H 21/04
[52] U.S. Cl. ................. 536/25.3; 435/6; 435/135; 435/145; 435/259
[58] Field of Search .................. 435/6, 135, 145, 435/259; 536/25.3

[56] References Cited

U.S. PATENT DOCUMENTS 5,118,603  6/1992  Popp et al. .................. 435/6

FOREIGN PATENT DOCUMENTS 145233  6/1985  European Pat. Off. .
89/03226  4/1989  WIPO .

OTHER PUBLICATIONS

Schweitz: "Action de l'eau oxygenee sur le DNA in presence d' ions ferreux et de lumiere", Biochimica et Biophysica Acta, vol 166, 1968.

Primary Examiner—Gary L. Kunz
Attorney, Agent, or Firm—Cushman Darby & Cushman IP Group Pillsbury Madison & Sutro LLP

[57] ABSTRACT

Peroxide, particularly supplied as hydrogen peroxide, is an effective nucleic acid degrading agent and can be used in the recovery of intracellularly produced materials from cell (particularly bacterial) lysates. The degradation or removal of nucleic acids from cell lysates is important because they form solutions of high viscosity which interfere with subsequent processing. Peroxide degradation is particularly useful in the recovery of polyhydroxyalkanoate polymers such as polyhydroxybutyrate/valerate from lysates of bacterial cells in which they are produced.

9 Claims, No Drawings

PEROXIDE DEGRADATION OF DNA FOR VISOCITY REDUCTION

This invention relates to the degradation of nucleic acids. Nucleic acid degradation is a useful or essential step in many processes involving products derived from biotechnology or fermentation processing generally.

An increasing number of valuable products are produced intracellularly, often in microbial cells, in industrial processes. To extract the product of interest, it is generally necessary to disrupt or lyse the host cells. One of the problems on such lysis is that, as well as the desired products, nucleic acids are released from the cells into the disruption medium. On being released, the nucleic acids uncoil and form networks in solution: this results in an increase in the viscosity of the cell lysate. This high viscosity can be a problem in downstream processing steps, as it can adversely effect mixing, solid/liquid separation, pumping and adsorption processes, to name but a few. Because of this property of nucleic acids, processes which involve cell disruption may require methods for breaking down nucleic acids, so as to enable subsequent processing steps to be carried out in an efficient manner or indeed at all.

There have been previous attempts in the prior art to degrade nucleic acids in industrial processes such as those described above. One possibility is to use heat, as is for example disclosed in EP-A-0145233, in which "heat shock" processes involve heating cells or a cell lysate to a temperature as high as 150° C. or more for a short period of time (generally a few seconds or minutes). While effective, this process is fairly energy-intensive and clearly requires the use of costly equipment if an aqueous medium is to be heated in liquid form significantly above 100° C.

Instead of using heat, nucleic acids can be degraded or removed (for example by precipitation) by the addition of chemical or biological agents. Nucleases are enzymes which hydrolyse nucleic acids and can be added to a cell lysate for that purpose. Purified preparations of nucleases, though, are expensive. A precipitating agent such as polyethylene imine may be significantly cheaper than a nuclease and may effectively remove the nucleic acid from the bulk of the cell lysate.

Although the chemical degradation of nucleic acids will be the route of choice in removing them from a cell lysate, there is a problem in finding a reagent that is effective, inexpensive and, importantly, leaves no detrimental residue after its use.

It has now been found that peroxide can be used as a particularly effective and suitable nucleic acid degrading agent, and it is to this finding that the present invention is addressed. It is believed that this nucleic acid degradation involves a substantial reduction in its molecular weight and that this reduces substantially the viscosity enhancing properties of the nucleic acid.

According to a first aspect of the present invention, there is provided a process of recovering a product from an aqueous preparation which comprises a quantity of nucleic acid sufficient to lead to a viscosity high enough to cause difficulty in a processing stage characterised by a step of degrading the nucleic acid by contacting it with a peroxide before or during the said stage.

According to a second aspect of the present invention, there is provided a process of degrading nucleic acid in a solution which comprises at least 0.1 g/litre, for example 0.5 to 20 g/litre of nucleic acid dissolved in water by contacting it with a peroxide.

According to a third aspect of the present invention, there is provided a process which comprises controlling the viscosity of an aqueous preparation which contains solid particles and at least 0.1 g/litre for example 0.5 to 10 g/litre of nucleic acid which comprises degrading nucleic acid with a peroxide and separating solid particles.

According to a fourth aspect of the present invention, there is provided a process of recovering a polysaccharide or preferably a polyhydroxyalkanoate polymer from cells which comprises degrading cellular material other than the said polymer in which in a first stage of degradation cellular material is degraded with a peroxide.

The nucleic acid may be any of the forms of nucleic acid found in cells. Both DNA and RNA degradation is therefore contemplated by the invention. Various forms of RNA may be implicated (for example, mRNA, tRNA and rRNA).

The aqueous preparation of nucleic acid may be a solution. However, in biological systems the nucleic acid may well be in association with proteins or other chemical species. The invention has particular application when the aqueous preparation of nucleic acid is a cell lysate, particularly a microbial cell lysate such as a bacterial cell lysate.

The peroxide may simply be hydrogen peroxide, or it may be a source of hydrogen peroxide. The source may for example be a peroxide salt or some other means of generating a peroxide anion of hydrogen peroxide in situ. Hydrogen peroxide is available as an aqueous solution, and it typically supplied as a 35% w/v aqueous solution. The concentration of peroxide used in the invention may be anything that is sufficient to effect the desired degree of degradation in an acceptable time period. For example, the concentration (expressed as hydrogen peroxide) may vary from 0.1 to 20% w/v. Usually the concentration will be in the range of 0.5 to 10% w/v, and often in practice the concentrations will be from 1 to 5% w/v.

The time and temperature of the incubation period are chosen so that nucleic acid degradation occurs to an acceptable degree. Generally speaking, the higher the temperature used, the less time is necessary for incubation. The upper limit of the temperature will be governed by the desire not to damage any biomolecule of interest and the need not to drive off or degrade significant amounts of hydrogen peroxide. The lower limit of the temperature will simply be governed by the kinetics of the reaction, as the degradation reaction velocity can be expected to decrease with temperature. As far as time is concerned, the upper limit of the incubation time till be determined by convenience, while the lower limit will be determined by the need to ensure sufficient length of incubation for appreciable amounts of nucleic acid to be degraded. Typical temperatures range from 5° to 100° C. and preferably 5° to 50° C., but will often be in the range of from 15° to 35° C. Temperatures around room temperature (20° to 25° C.) may be useful in practice. Typical reaction times may last from 5 minutes to 5 days, largely depending on the temperature, but will often in practice be from 1 hour to 2 days. An incubation period of from 10 to 20 hours may be preferred in practice. One combination that has been found to be quite effective is a 16 hour reaction period at room temperature. However, if shorter reaction times are desired higher temperatures, for example up to 90° C. may be preferred.

If, in accordance with the invention, peroxide is being used to degrade nucleic acid in a cell lysate, the peroxide may be used in conjunction with a cell lysing agent. Suitable cell lysing agents include surfactants, particularly anionic surfactants such as sodium dodecyl sulphate (SDS). Alternatively, the peroxide could be added after a cell preparation has been lysed with an appropriate agent. The concentration of the cell lysing agent to be used will of course depend on its nature, but as guidance SDS may be used in concentrations of from 0.1 to 20% w/v, for example 0.5 to 20% w/v and typically from about 1 to 5% w/v. If no cell lysing agent is employed it is preferred that the cells should be subjected to elevated temperatures preferably sufficient to denature any proteins present which would catalyse peroxide decomposition. By this means the quantity of peroxide to be supplied to the process may be reduced.

The pH of the aqueous environment is not believed to be particularly critical, but in an aqueous preparation derived from microbial or other cells will generally be about neutral. As the invention is not believed to be particularly pH-sensitive, though, a pH range of from 4 to 9 may be suitable in practice, although generally the pH will be in the 6 to 8 range.

The invention has particular application, as indicated above, in the extraction of material produced intracellularly. Often, it will be desired to extract a compound from bacterial or other microbial cells; the usefulness of the invention is however not restricted to macromolecular recovery. The invention has particular application in the extraction of biopolymers including polyhydroxyalkanoates such as polyhydroxybutyrate (PHB) and polyhydroxybutyrate/valerate (PHB/V) copolymer. Polyhydroxyalkanoate polymers can be produced, either naturally or by induction, in a variety of natural or engineered organisms, particularly bacterial or other microorganisms, for example of the genera Alcaligenes, Athiorhodium, Azotobacter, Bacillus, Nocardia, Pseudomonas, Rhizobium and Spirillum. Preferred polyhydroxyalkanoate production species include *Alcaligenes eutrophus, Hydrogenomonas eutropha* H-16, *Alcaligenes latus* and various Pseudomonas spp. Among the copious references in the literature to the production of polyhydroxyalkanoate polymers may be included EP-A-0069497, U.S. Pat. No. 4,101,533, EP-A-0144017, EP-A-0145233 and EP-A-0392687.

The use of peroxides such as hydrogen peroxide as nucleic acid degradating agents in the extraction of polyhydroxyalkanoates has the advantage that nucleic acid degradation may take place at relatively low temperatures, such as about 20° C.: as well as representing an energy saving over prior heat-shock processes, the polyalkanoate polymer may well be damaged less at lower temperatures. The proteolytic enzyme and/or detergent solubilisation and/or other steps described in EP-A-0145233 may then be used, as described in that document.

According to a fifth aspect of the invention, there is provided the use of peroxide as a nucleic acid degrading agent. Preferred features of the second aspect of the invention are as for the first aspect, *mutatis mutandis*.

The invention will now be illustrated by the following examples.

EXAMPLE 1

A strain of *Alcaligenes eutrophus* was grown in batch culture in an aqueous medium of a mixture of glucose and propionic acid under phosphorus limitation to give a culture containing 101 g/l cells containing 71% of a hydroxybutyrate (HB)/3-hydroxyvalerate (HV) copolymer with a molar hydroxyvalerate content of 11% (the remainder of the polymer being hydroxybutyrate).

A sample of the cells containing the PHB/V copolymer was washed three times in demineralised water using centrifugation. The suspension viscosity, measured by a Bohlin VOR rheometer (in concentric cylinder mode) was measured to be 1.8 mPa.s as 580/sec.

A 2% w/v addition of SDS at pH 7 was used to lyse the cells. This resulted in a marked increase in the suspension viscosity to 90 mPa.s at 580/sec, measured in the same apparatus. Sufficient 35% w/v $H_2O_2$ was added to give a concentration in solution of 3% w/v. After 16 hours at 20° C. the viscosity of the suspension was again measured, and determined to be 2.5 mPa.s at 580/sec, which is close to the value of the original pre-lysis suspension.

COMPARISON EXAMPLE

The procedure of the above Example was repeated, except that the hydrogen peroxide was not added. Instead, the cell lysate was allowed to stand for 16 hours at 20° C. without any addition after the SDS. The viscosity at the end of this time was 50 mPa.s at 580/sec, which although decreased from the initial post-lysis value does not represent a major reduction in the viscosity for practical purposes.

EXAMPLE 2

Strain NCIMB40124 of *Alcaligenes eutrophus* was grown in a fermenter of 90m³ working volume. The culture was inoculated into a medium containing the following (concentrations in g/l, pH7 and 30° C.):

| | |
|---|---|
| $MgSO_4.7H_2O$ | 2.2 |
| $K_2SO_4$ | 3.0 |
| $Na_2.SO_4$ | 0.18 |
| $FeSO_4.7H_2O$ | 0.18 |
| Glucose | 13.0 |
| Trace Elements | 3.0 (mls) |
| Phosphoric Acid | 6.5 (mls of 1.1M) |

After 24 hours when the phosphate content of the medium had become limiting, glucose and propionic acid were fed to the fermenter at rates of 300 kg/hr and 54 kg/hr respectively, for a further 48 hours. After this time the cells were harvested.

This gave a culture containing 145 g/l cells with a content of 75.4% 2-hydroxybutyrate (HB)/3-hydroxyvalerate (HV) copolymer with a molar hydroxyvalerate content of 9% (the remainder of the polymer being hydroxybutyrate). The cells contained 3% nucleic acid.

The pH of the culture was adjusted to 7 with "880" ammonium hydroxide and SDS added to give a concentration of 3%. A marked increase in the viscosity of the culture occurred. Hydrogen peroxide solution (35% w/v) was added to the culture to give a concentration of 6% w/v. The culture was stirred for 16 hours at room temperature. After this time the culture was washed by centrifuging and resuspending 5 times with demineralised water. The culture was then treated with hydrogen peroxide at a concentration of 5% w/v at 80° C. for 3 hours. The now purified HB/HV copolymer was washed 3 times in demineralised water and oven dried at 60° C. for 24 hours. Losses of the copolymer were judged to be low as assessed by the turbidity of the centrate.

The Yellowness Index (YI) of the polymer was measured by ASTM method D1925-70 and found to be 30.

This indicates a protein content of about 0.4% and the total material is considered to be at least 99% copolymer. The product was substantially odour free. The molecular weight was in excess of 900,000 Daltons. It is therefore considered to be a product of high purity and high molecular weight which is very suitable for use as a plastics material.

I claim:

1. In a process of recovering a product from an aqueous preparation which comprises a quantity of nucleic acid sufficient to lead to a viscosity high enough to cause difficulty in a processing stage, wherein the improvement is degrading the nucleic acid by contacting it at a temperature in the range of 15° to 35° C. with a peroxide before or during the said stage, the peroxide being used in sufficient amount to degrade the nucleic acid and reduce the viscosity of said aqueous preparation to facilitate the processing thereof to recover the product therefrom.

2. A process which comprises controlling the viscosity of an aqueous preparation which contains solid particles and at least 0.1 g/litre to 10 g/litre of nucleic acid which comprises degrading nucleic acid at a temperature in the range of 15° to 35° C. with a peroxide in amount sufficient to reduce the viscosity of said preparation and separating solid particles from said preparation of reduced viscosity.

3. A process as claimed in claim 1, in which a polyhydroxyalkanoate is separated from the preparation after the reduction in viscosity.

4. A process as claimed in claim 3, wherein the aqueous preparation is a cell lysate and the peroxide is hydrogen peroxide.

5. A process as claimed in claim 3, wherein the preparation is prepared by lysing cells with an anionic surfactant.

6. A process of recovering a polyhydroxyalkanoate or polysaccharide polymer from admixture thereof with cells which comprises degrading cellular material other than the polymer in said admixture by contacting said cellular material with a peroxide at a temperature in the range of from 15° to 35° C. whereby said cellular material is degraded and the viscosity of said admixture is reduced, and thereafter recovering said polymer from said admixture.

7. A process as claimed in claim 6, wherein the peroxide is supplied as hydrogen peroxide.

8. A process as claimed in claim 1, wherein the pH is from 6 to 8.

9. A process as claimed in claim 3, wherein the polyhydroxyalkanoate polymer is a polyhydroxybutyrate/valerate polymer.

* * * * *